(12) United States Patent
Guala

(10) Patent No.: US 10,537,726 B2
(45) Date of Patent: Jan. 21, 2020

(54) TUBULAR FITTING FOR MEDICAL FLUID LINES

(71) Applicant: Industrie Borla S.p.A., Moncalieri (Turin) (IT)

(72) Inventor: Gianni Guala, Turin (IT)

(73) Assignee: Industrie Borla S.p.A., Moncalieri (Turin) (IT)

(*) Notice: Subject to any disclaimer, the term of this patent is extended or adjusted under 35 U.S.C. 154(b) by 0 days.

(21) Appl. No.: 16/184,539

(22) Filed: Nov. 8, 2018

(65) Prior Publication Data

US 2019/0076641 A1 Mar. 14, 2019

Related U.S. Application Data

(63) Continuation of application No. 15/311,056, filed as application No. PCT/IB2014/063278 on Jul. 21, 2014, now Pat. No. 10,155,103.

(30) Foreign Application Priority Data

May 12, 2014 (IT) .............................. TO2014A0371

(51) Int. Cl.
*A61M 5/14* (2006.01)
*A61M 39/10* (2006.01)
(Continued)

(52) U.S. Cl.
CPC .... *A61M 39/1011* (2013.01); *A61M 39/1055* (2013.01); *A61M 39/22* (2013.01);
(Continued)

(58) Field of Classification Search
CPC .......... A61M 2039/1033; A61M 39/10; A61M 39/26; A61M 2039/268;
(Continued)

(56) References Cited

U.S. PATENT DOCUMENTS

| 5,620,427 A | 4/1997 | Werschmidt |
| 6,152,913 A | 11/2000 | Feith |

(Continued)

FOREIGN PATENT DOCUMENTS

| DE | 4318101 A1 | 12/1994 |
| EP | 0633038 A1 | 1/1995 |

(Continued)

OTHER PUBLICATIONS

International Search Report for International Application No. PCT/IB2014/063278, dated Jan. 8, 2015.

(Continued)

*Primary Examiner* — Jason E Flick
(74) *Attorney, Agent, or Firm* — Heslin Rothenberg Farley & Mesiti P.C.; Victor A. Cardona, Esq.

(57) ABSTRACT

A tubular fitting for medical fluid lines includes a hollow body within which a male connector and an opposite female connector are coaxially housed. The male connector is coupled in rotation with respect to the body in a direction corresponding to a screwing with a female connector of the line, while it is normally freely rotatable in the unscrewing direction, in the same way as the female connector is coupled in rotation with respect to the body in the direction corresponding to the screwing with a male connector of the line, while it is normally freely rotatable in the unscrewing direction. The male connector and/or the female connector can possibly be locked in rotation with respect to the body in the unscrewing direction, only following a positive command.

17 Claims, 16 Drawing Sheets

(51) Int. Cl.
*A61M 39/26* (2006.01)
*A61M 39/22* (2006.01)

(52) U.S. Cl.
CPC ..... *A61M 39/26* (2013.01); *A61M 2039/1016* (2013.01); *A61M 2039/1033* (2013.01); *A61M 2205/0216* (2013.01)

(58) Field of Classification Search
CPC .. A61M 2039/1016; A61M 2205/0216; A61M 39/1011; A61M 39/1055; A61M 39/22
USPC .......................................................... 604/256
See application file for complete search history.

(56) References Cited

U.S. PATENT DOCUMENTS

| | | |
|---|---|---|
| 7,588,563 B2 | 9/2009 | Guala |
| 7,666,170 B2 | 2/2010 | Guala |
| 8,721,628 B2 | 5/2014 | Ziman |
| 8,968,271 B2 | 3/2015 | Guala |
| 2004/0238776 A1 | 12/2004 | Peters |
| 2007/0043334 A1 | 2/2007 | Guala |
| 2007/0088327 A1* | 4/2007 | Guala ................... A61M 39/10 604/533 |
| 2009/0292274 A1 | 11/2009 | Guala |
| 2012/0271246 A1 | 10/2012 | Guala |
| 2013/0187381 A1* | 7/2013 | Guala ................... A61M 39/10 285/387 |
| 2016/0106967 A1 | 4/2016 | Guala |

FOREIGN PATENT DOCUMENTS

| | | |
|---|---|---|
| EP | 1747796 A1 | 1/2007 |
| EP | 1747797 A1 | 1/2007 |
| JP | 2013-526398 A | 6/2013 |
| JP | 2013-150805 A | 8/2013 |
| WO | 2011/145991 A1 | 11/2011 |

OTHER PUBLICATIONS

May 8, 2018 Office Action (English Translation) for corresponding Japanese patent application No. 2016-567487.
May 8, 2018 Notification of Reasons for Rejection (English Translation) for corresponding Japanese patent application No. 2016-567487.

* cited by examiner

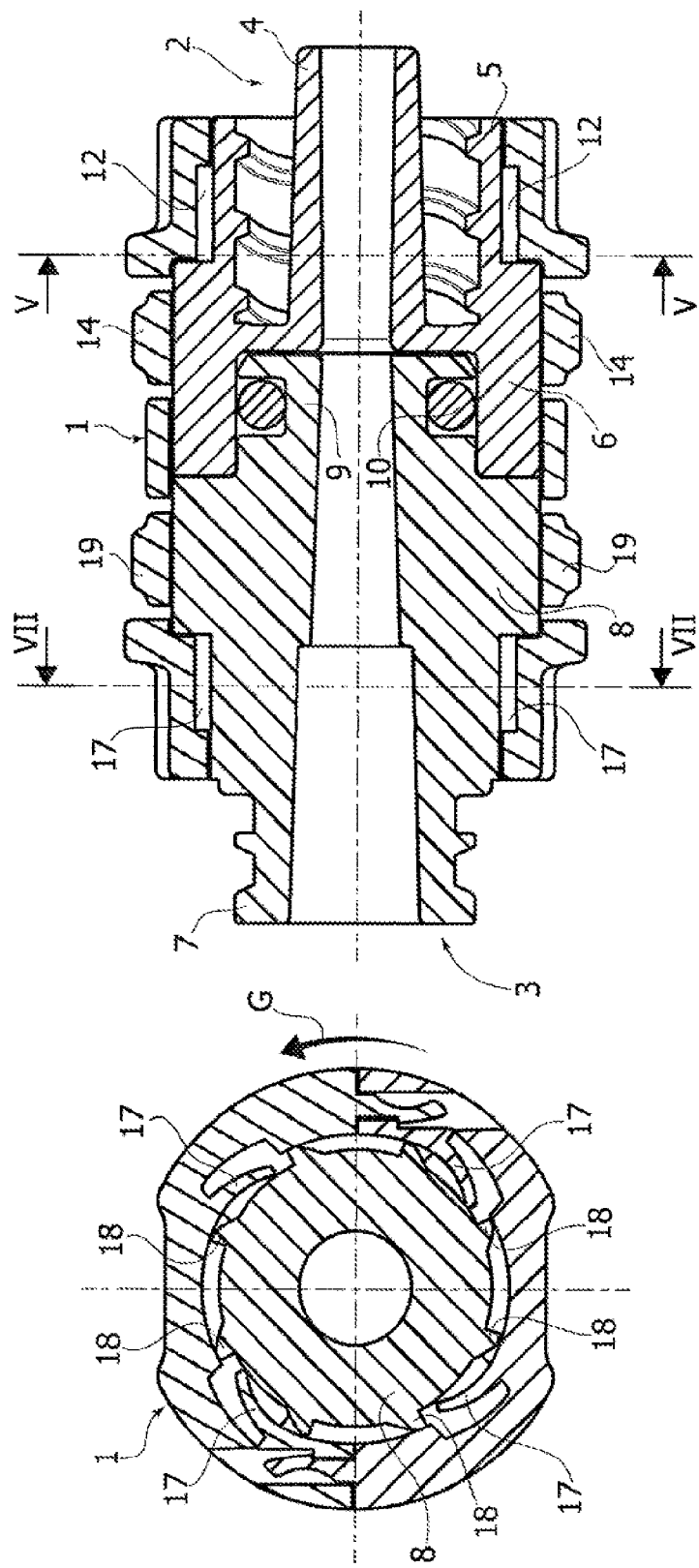

TUBULAR FITTING FOR MEDICAL FLUID LINES

CROSS REFERENCE TO RELATED APPLICATIONS

This application is a continuation of U.S. patent application Ser. No. 15/311,056, filed Nov. 14, 2016, which is a national stage filing under section 371 of International Application No. PCT/IB2014/063278, filed on Jul. 21, 2014, and published in English on Nov. 19, 2015, as WO 2015/173612 A1, and which claims priority of Italian application No. TO2014A000371 filed on May 12, 2014, the entire disclosure of these applications being hereby incorporated herein by reference.

FIELD OF THE INVENTION

The present invention relates, in general, to medical fluid lines, for example, hemodialysis lines, chemotherapy lines and the like.

STATE OF THE ART

Such fluid lines are normally fitted along their path with connectors for the connection between the various components of the line: typically male and female luer lock connectors and the like. Accidental disengagement or due to incorrect maneuvers between these connectors can result in possible serious consequences for the patients connected during the use of the line.

SUMMARY OF THE INVENTION

The object of the present invention is to provide a safe and effective solution to this problem, whilst at the same time being practical and functional.

According to the invention, this object is achieved thanks to a fitting for medical fluid lines comprising a hollow body within which a male connector accessible at one end of the body and a female connector accessible at the other end of the body, are coaxially housed. The fitting comprises first unidirectional coupling means for locking in rotation the male connector with respect to the body in the direction corresponding to the screwing between said male connector and a complementary female connector of the line, and to enable free rotation of the male connector in the opposite direction, and second unidirectional coupling means for locking in rotation the female connector with respect to the body in the direction corresponding to the screwing between said female connector and a complementary male connector of the line, and to enable free rotation of the female connector in the opposite direction.

Thanks to this solution idea, the fitting according to the invention is advantageously usable in the form of an intermediate element for a secure connection between a male connector and a female connector of medical fluid lines. In practice, these connectors, instead of being connected directly to each other, are thus connected indirectly, by means of the fitting according to the invention, which ensures the necessary degree of safety against risks of undesired openings of the medical line due to accidental decoupling or a wrong maneuver between the connectors of the line.

According to a further advantageous characteristic of the invention, first and/or second locking means can also be provided, designed to be positively operated to lock in rotation the male connector and/or the female connector, respectively, with respect to the body in the aforesaid opposite direction of rotation.

In the fitting according to the invention, the male and female connectors can be in communication with each another to define a flow passage through the fitting, or the communication between the male and female connectors can be obstructed.

Furthermore, according to a particularly advantageous embodiment of the invention, the female connector can be a valve connector and the male connector can also be a valve connector.

BRIEF DESCRIPTION OF THE DRAWINGS

The invention will now be described in detail with reference to the accompanying drawings, provided purely by way of non-limiting example, in which:

FIG. 3 is an axial section view along the line III-III of FIG. 2, FIG. 7 is a cross sectional view along the line VII-VII of FIG. 3.

DETAILED DESCRIPTION OF THE INVENTION

Figure 1:
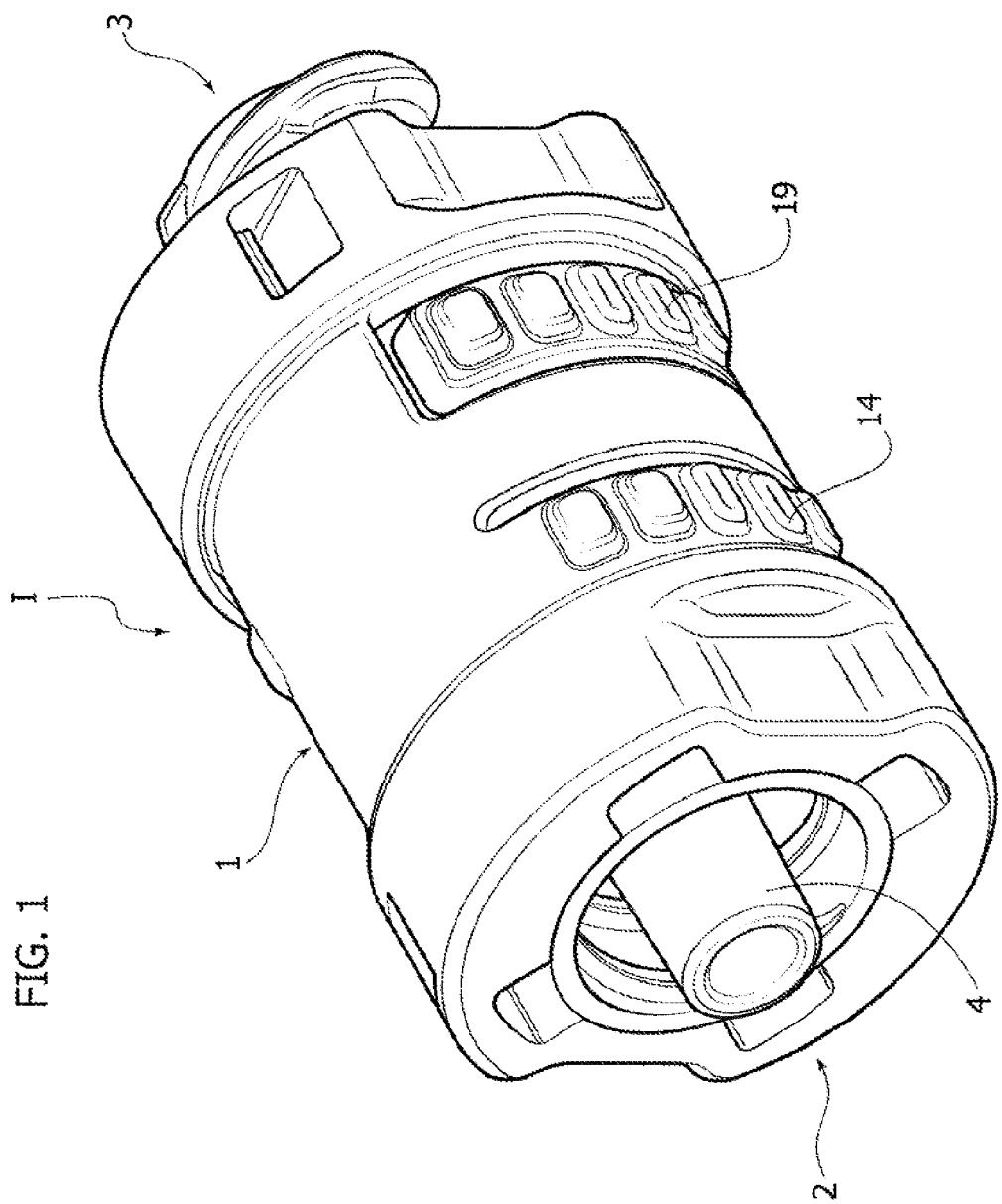
FIG. 1 is a schematic perspective view of a fitting for medical fluid lines according to a first embodiment of the invention.
Figure 2:
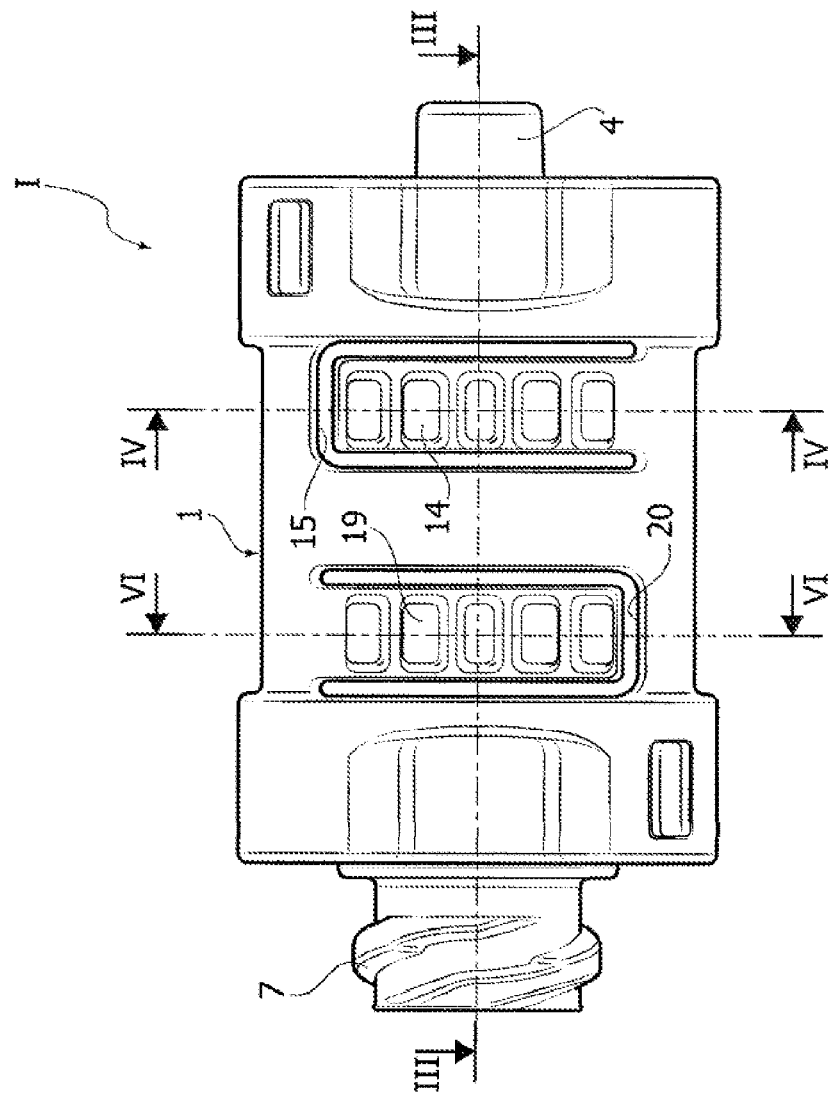
FIG. 2 is an elevational side view of the fitting.

Referring initially to FIGS. 1 to 7, the fitting according to a first embodiment of the invention is indicated with I and is tubular. It comprises an outer hollow body 1 of generally cylindrical shape, within which a male connector 2 of the luer lock type and analogues, and a female fitting 3 of the luer lock type and analogues are coaxially housed in an opposite condition.

The connectors 2 and 3 are rotatably mounted relative to the body 1 and to each another, with the limitations which will be discussed, and have a generally conventional shape. In detail, the male connector 2 comprises an inner tubular element 4 with a conical outer surface protruding from one end of the body 1, and an internally threaded outer hollow element 5, which extends towards the inside of the body 1 with a hollow appendage 6.

The female connector 3 consists of an externally threaded tubular element 7 with a conical inner surface, protruding from the other end of the body 1 and integrally formed with an appendage 8 terminating with a shank 9 rotatably inserted within the hollow appendage 6 of the male connector 2.

The connectors 2 and 3 are locked axially within the body 1, which is conveniently formed from two half-shells coupled together in an interlocking manner, and an O-ring seal 10 is interposed between the shank 9 and the hollow appendage 6.

The male and female connectors 2, 3 define a free flow passage through the connector according to the invention, and during use are intended to be respectively coupled to a complementary female connector and to a complementary male connector of a medical line.

The hollow appendage 6 of the male connector 2 and the appendage 8 of the female connector 3 are locked axially within the hollow body 1 and are coupled with this in rotation in one direction and normally freely rotatable in the opposite direction. However, as will become evident, the rotation in the opposite direction may also possibly be locked, but only following a positive command imparted manually.

Figure 4:
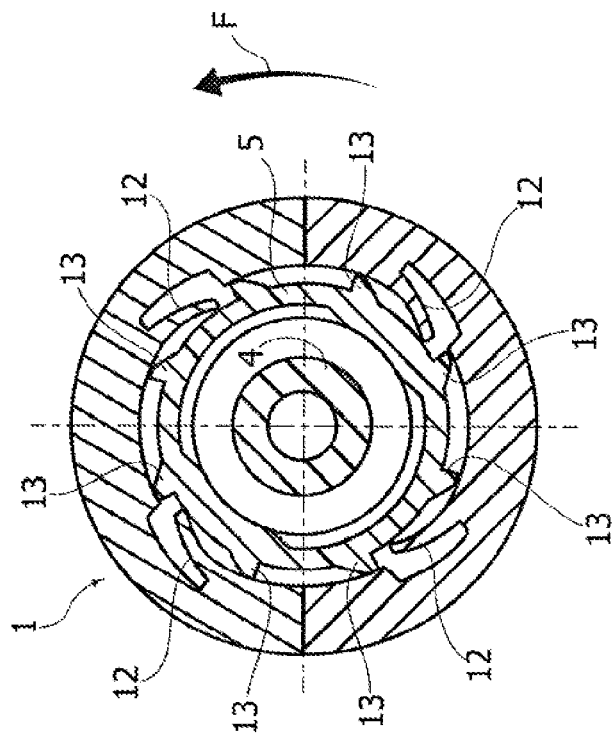
FIG. 4 is a cross sectional view along the line IV-IV of FIG. 2.
Figure 5:
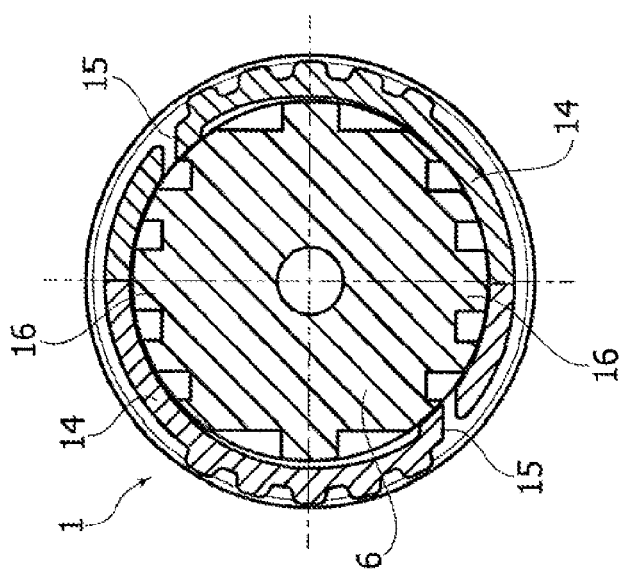
FIG. 5 is a cross sectional view along the line V-V of FIG. 3.
Figure 8:
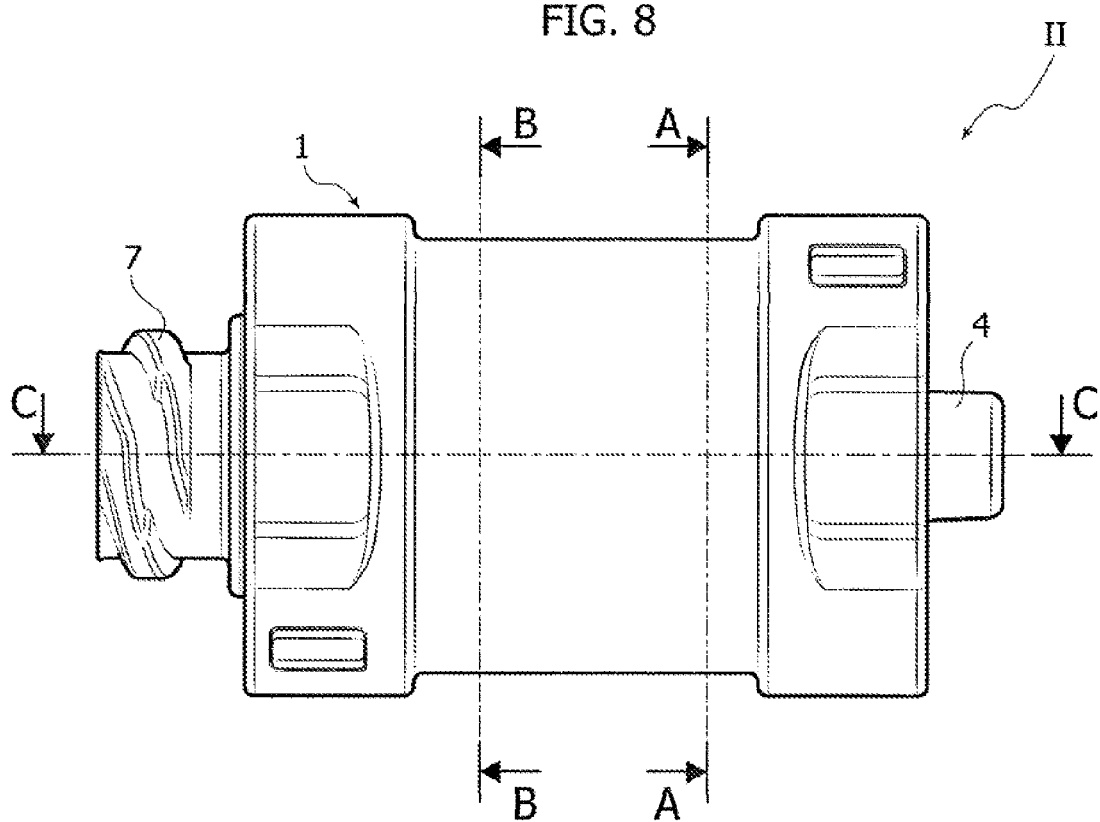
FIG. 8 is an elevational side view of a second embodiment of the fitting according to the invention.
Figure 9:
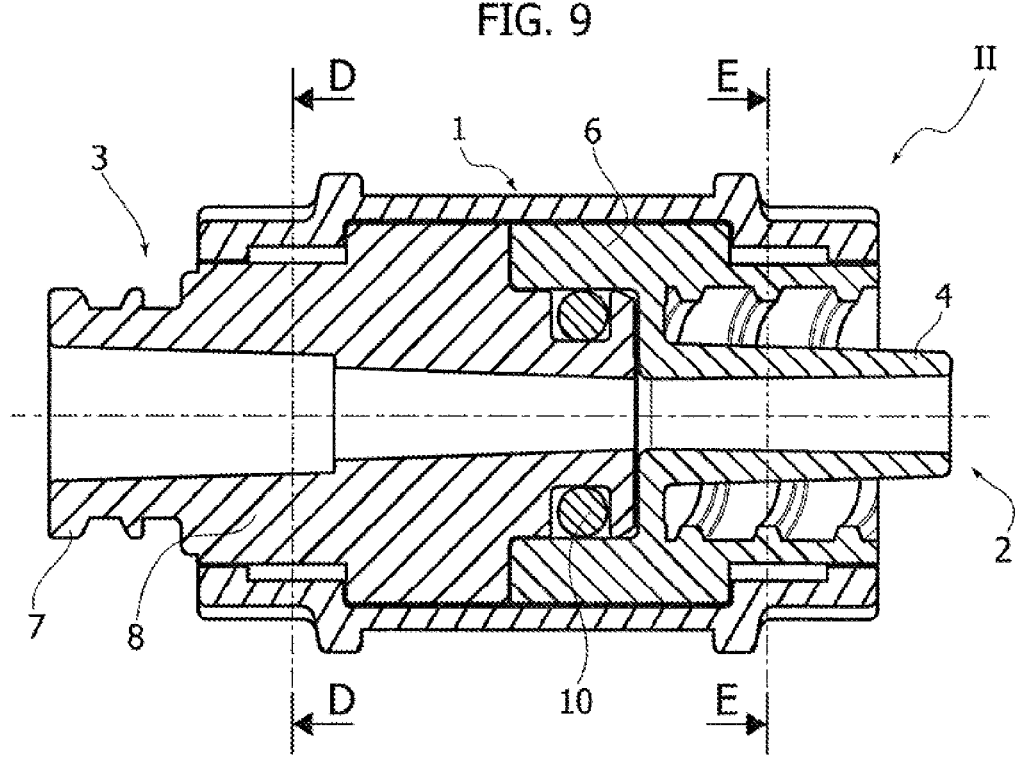
FIG. 9 is an axial section view according to the line C-C of FIG. 8.
Figure 10:
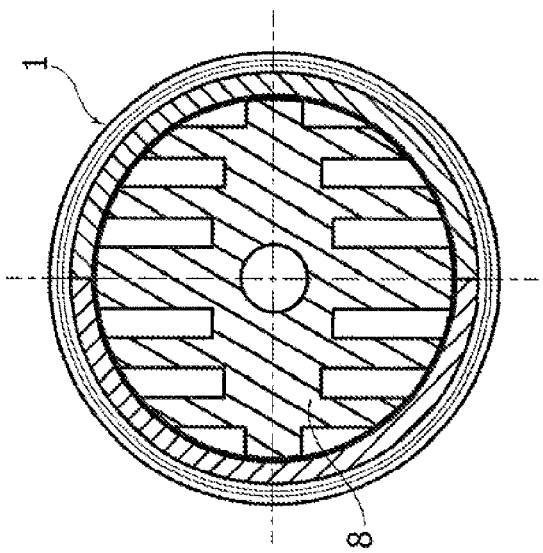
FIG. 10 is a cross sectional view along line B-B of FIG. 8.
Figure 11:
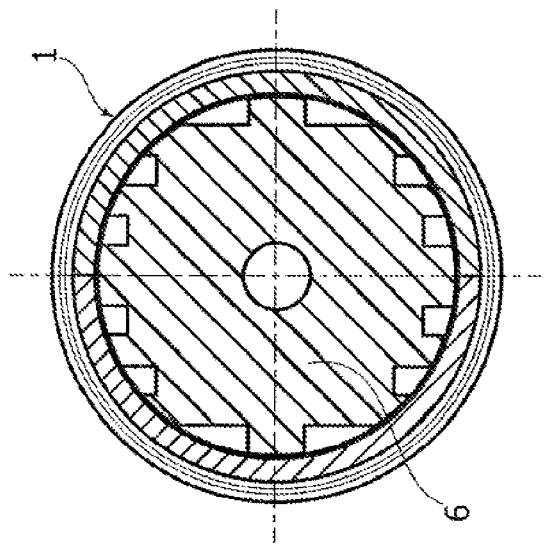
FIG. 11 is a cross sectional view along line A-A of FIG. 8.
Figure 12:
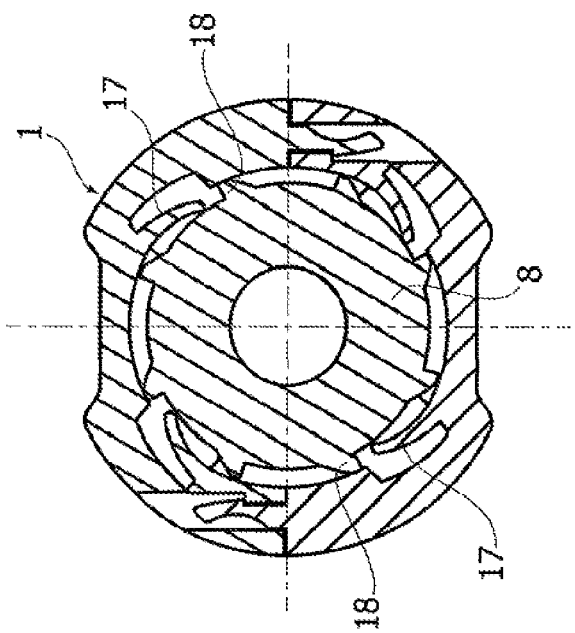
FIG. 12 is a cross sectional view along line D-D of FIG. 9.
Figure 13:
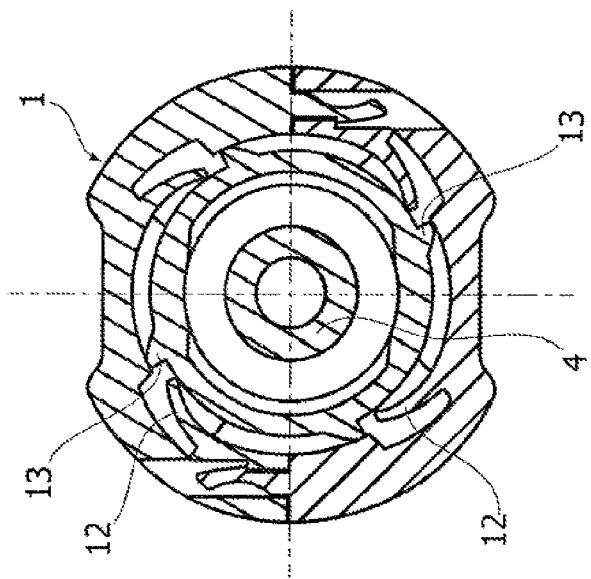
FIG. 13 is a cross sectional view along line E-E of FIG. 9.
Figure 14:
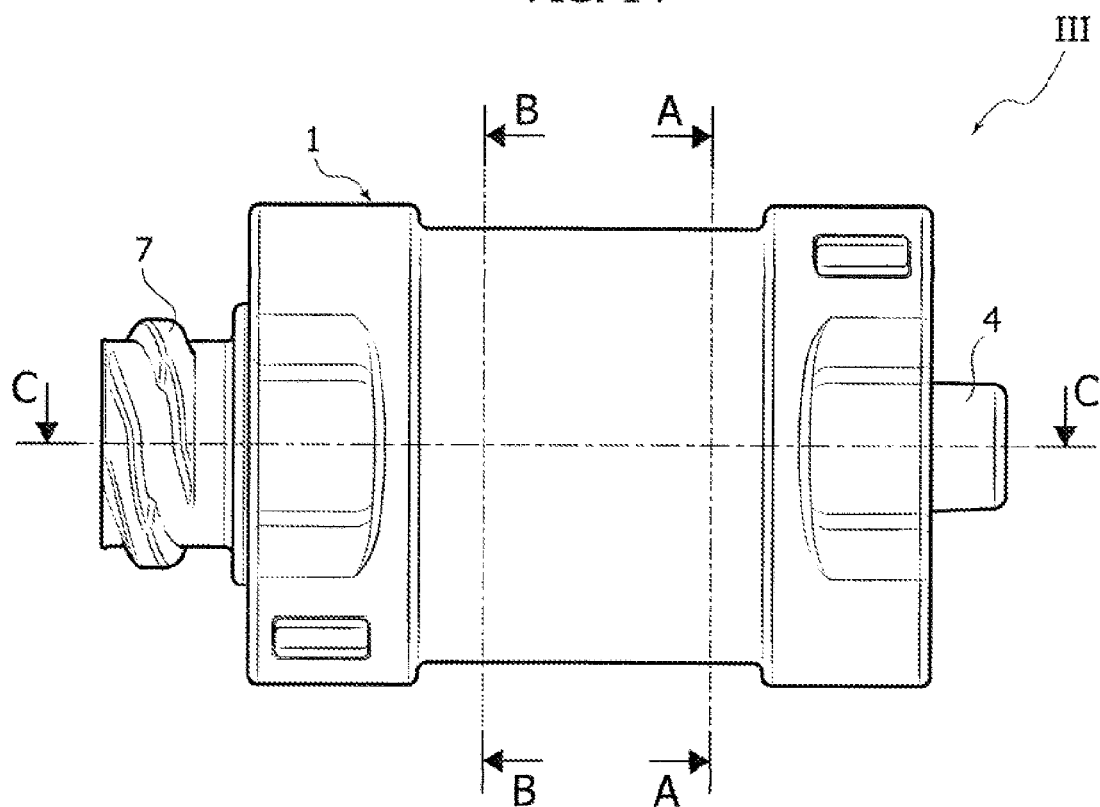
FIG. 14 is an elevational side view of a third embodiment of the fitting according to the invention.
Figure 15:
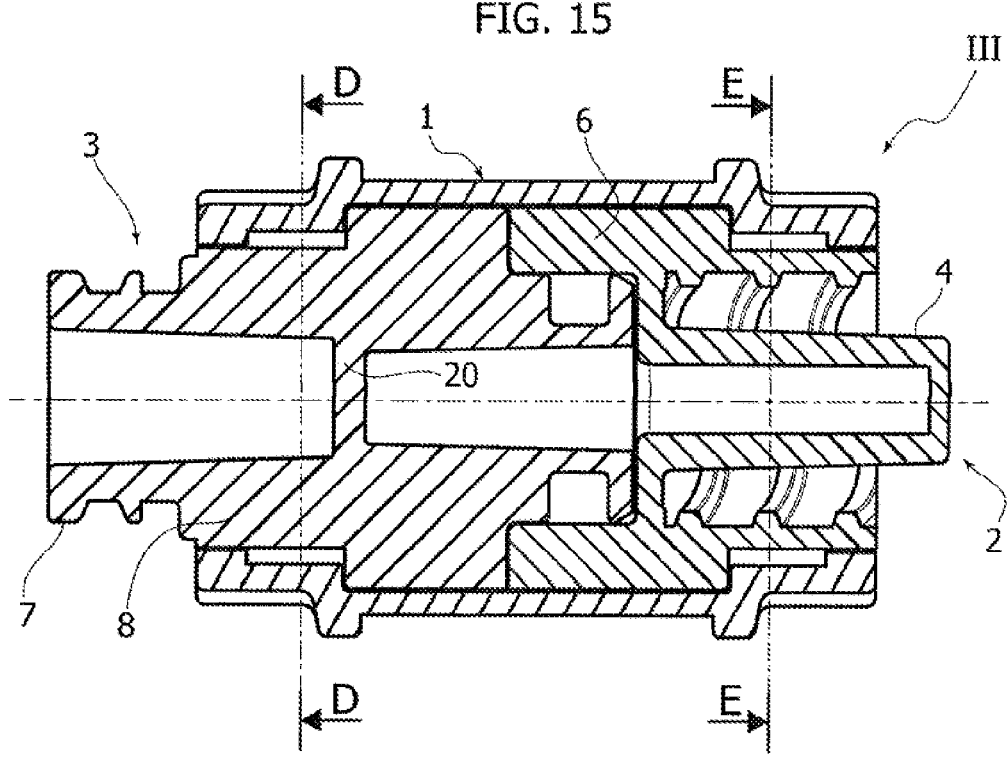
FIG. 15 is an axial section view according to the line C-C of FIG. 14.
Figure 17:
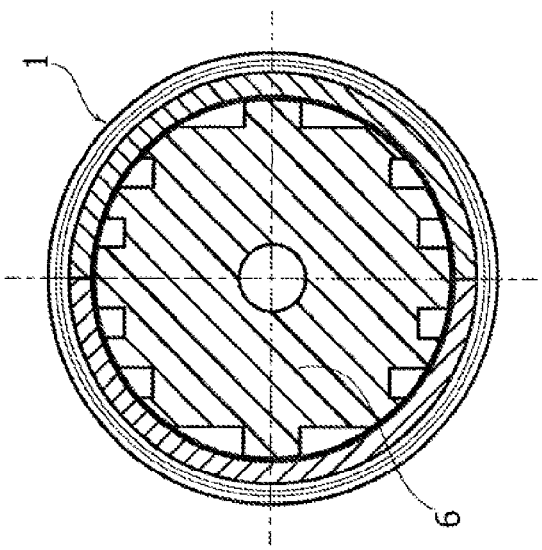
FIG. 17 is a cross sectional view along line A-A of FIG. 14.
Figure 16:
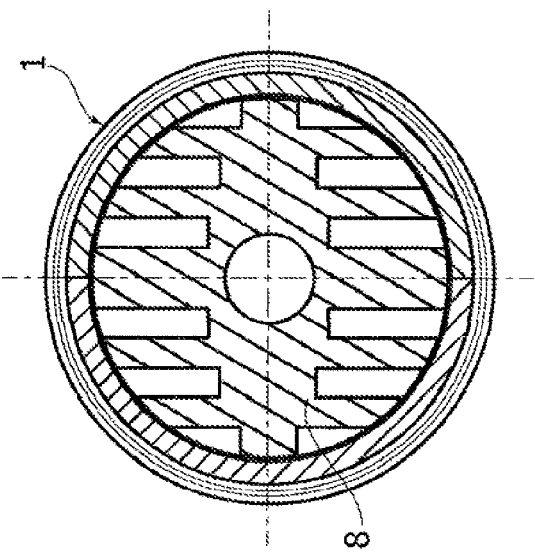
FIG. 16 is a cross sectional view along line B-B of FIG. 14.
Figure 18:
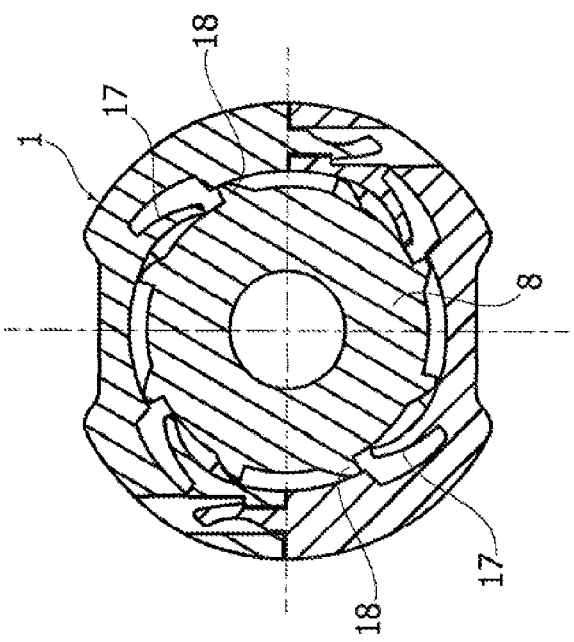
FIG. 18 is a cross sectional view along line D-D of FIG. 15.
Figure 19:
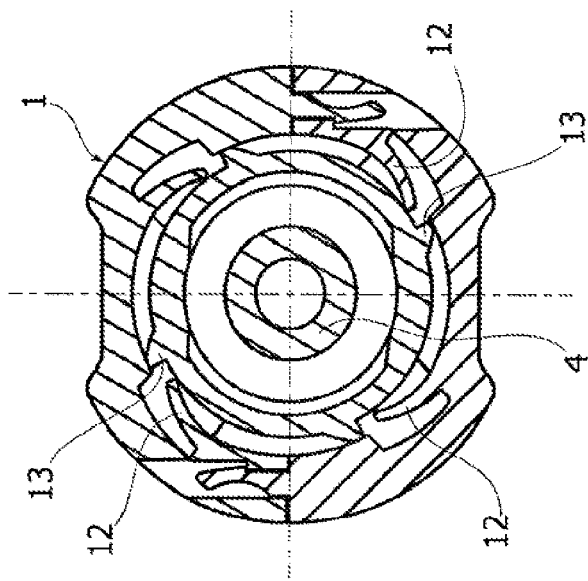
FIG. 19 is a cross sectional view along line E-E of FIG. 15.
Figure 20:
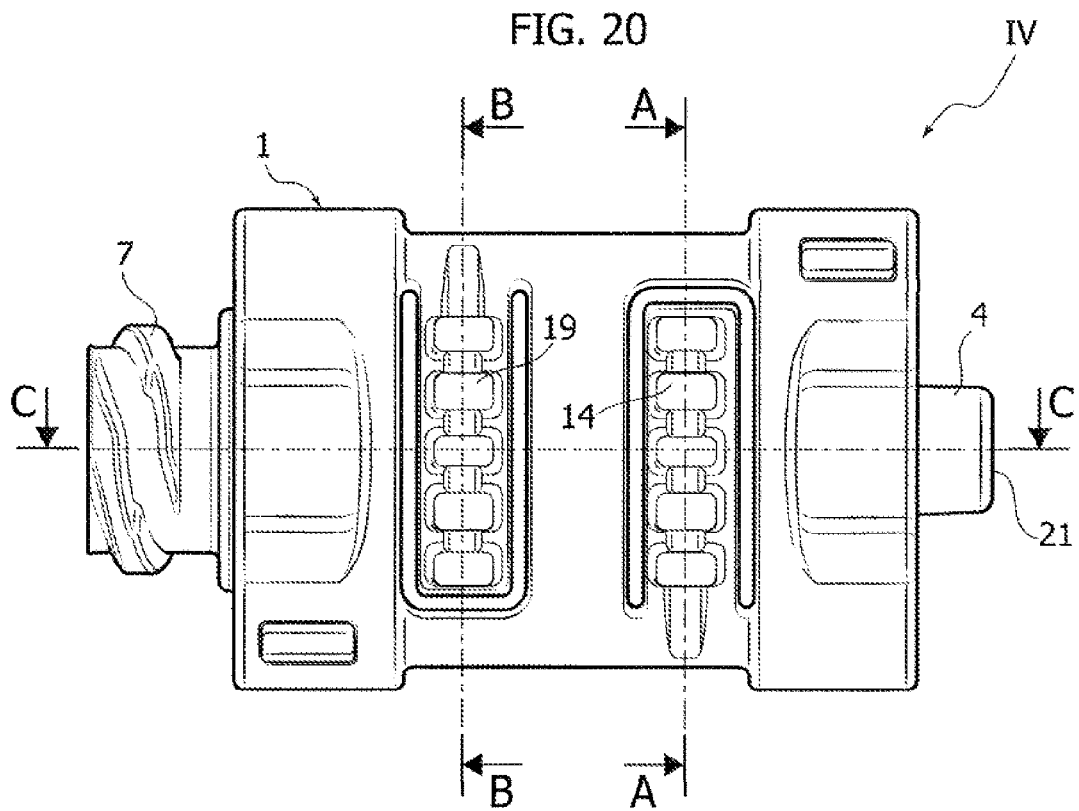
FIG. 20 is an elevational side view of a fourth embodiment of the fitting according to the invention.

In detail, and referring now to FIGS. 4 and 5, the hollow body 1 is formed internally, on the side of the male connector 2, of a crown of elastically yielding ratchet teeth 12 cooperating by unidirectional coupling with corresponding projecting teeth 13 formed on the outside of the hollow element 5 of the male connector 2. The arrangement is such so that the hollow element 5, and therefore the entire male connector 2, is coupled in rotation with the hollow body 1 in the direction indicated by the arrow F in FIG. 5, due to the effect of the engagement between the teeth 12 and 13. The direction of rotation F corresponds to the screwing between the male connector 2 and a complementary female connector, assuming the hollow body 1 is kept stationary, and then the complementary female connector is rotated to screw it into the male connector 2. In the opposite direction of rotation, or rather, the unscrewing direction, the male connector 2 is freely rotatable relative to the hollow body 1 due to the bounce of the yielding teeth 12 on the teeth 13, so that the complementary female connector cannot unscrew itself.

Obviously, in the case in which the hollow body 1 rotates and the complementary female connector is kept stationary, the situation is reversed, i.e. the direction of screwing is opposite to that of the arrow F, and the unscrewing direction is that of the arrow F.

In this way, during use, an accidental disengagement or wrong maneuver between the male connector 2 and the complementary female connector is prevented. The unscrewing may, however, possibly be allowed, but, as mentioned, only a result of a positive maneuver. To this effect, the wall of the hollow body 1 may also be formed with a pair of elastically yielding locking segments 14 whose free ends 15 are suitable for engaging, as a result of a thrust applied to the segments 14, respective peripheral teeth formations 16 of the hollow appendage 6 (FIG. 4), so as to lock the rotation of the male connector 2 with respect to the body 1.

Figure 6:
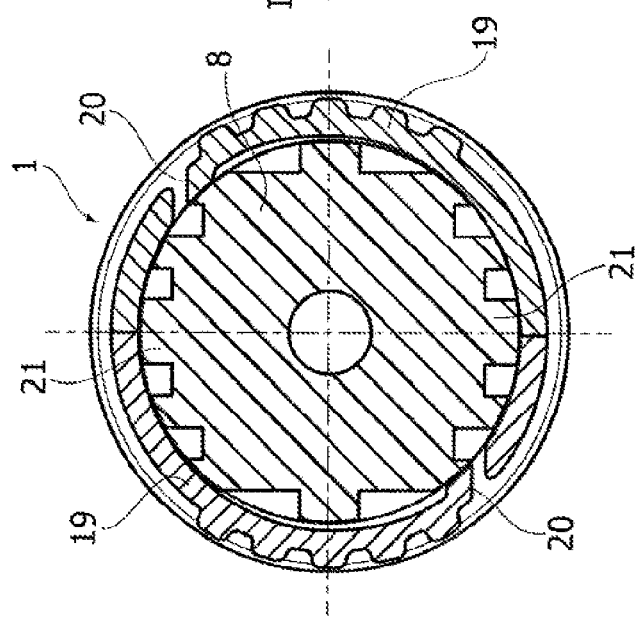
FIG. 6 is a cross sectional view along the line VI-VI of FIG. 2.

Similarly, and with reference to FIGS. 6 and 7, the female connector 3 is coupled in rotation with the hollow body 1 in the direction indicated by the arrow G in FIG. 7, corresponding to the screwing of this female connector 3 with a complementary male connector, maintaining the hollow body 1 stationary, while it is normally freely rotatable in the opposite direction, i.e. the unscrewing direction. To this effect, the hollow body 1 is formed with a further series of elastically yielding ratchet teeth 17, analogous to the yielding teeth 12, cooperating by unidirectional coupling with corresponding projecting teeth 18 formed on the outside of an initial portion of the appendage 8. For possible locking of the female connector 3 in rotation with respect to the hollow body 1, in the direction opposite to that indicated by the arrow G, a positive command manual should also be imparted in this case, and to this effect, the hollow body 1 can be formed with a further pair of elastically yielding locking segments 19, analogous to the yielding locking segments 14, the free ends 20 of which are suitable for engaging respective peripheral teeth formations 21 of the appendage 8 (FIG. 6).

During use, the fitting according to the invention advantageously operates in the manner of an intermediate safety element for the coupling of the female connector with the male connector of a medical fluid line, which as already mentioned are connected, instead of directly to each other, to the male connector 2 and the female connector 3, respectively. Following this connection, an accidental opening or due to incorrect operation of the medical line is thus reliably prevented, as the separation between the female connector of the line and the male connector 2 cannot be operated, or if at all, can only be operated voluntarily by applying a manual pressure on the elastically yielding segments 14, if present, and similarly, the separation between the male connector of the line and the female connector 3 can possibly be achieved only by pressing the elastically yielding segments 19, if present.

The further embodiments of the fitting according to the invention differ from the one already described only in the differences that will now be described in detail, using the same numerical references (partly omitted for simplicity of illustration) for the identical or similar parts.

In the variant shown in FIGS. 8-13, the fitting, indicated as a whole with II, tubular in this case as well, to define an open flow line, essentially differs from the fitting I of FIGS. 1-7 only in the fact that the outer body 1 is devoid of yielding locking segments 14 and/or 19. Therefore, the fitting II does not allow the voluntary unscrewing of the male connector 2 and/or the female connector 3 from the relative complementary female and male connectors.

In the variant shown in FIGS. 14-19, the fitting, indicated as a whole with III, is analogous to the fitting II and only differs from it in the fact that it is not tubular, or rather it does not define an open flow passage between the two connectors 2 and 3. The communication between the two connectors is permanently obstructed: to this effect, the female connector 3 has a transverse obstructive partition 20 (FIG. 21).

Figure 21:
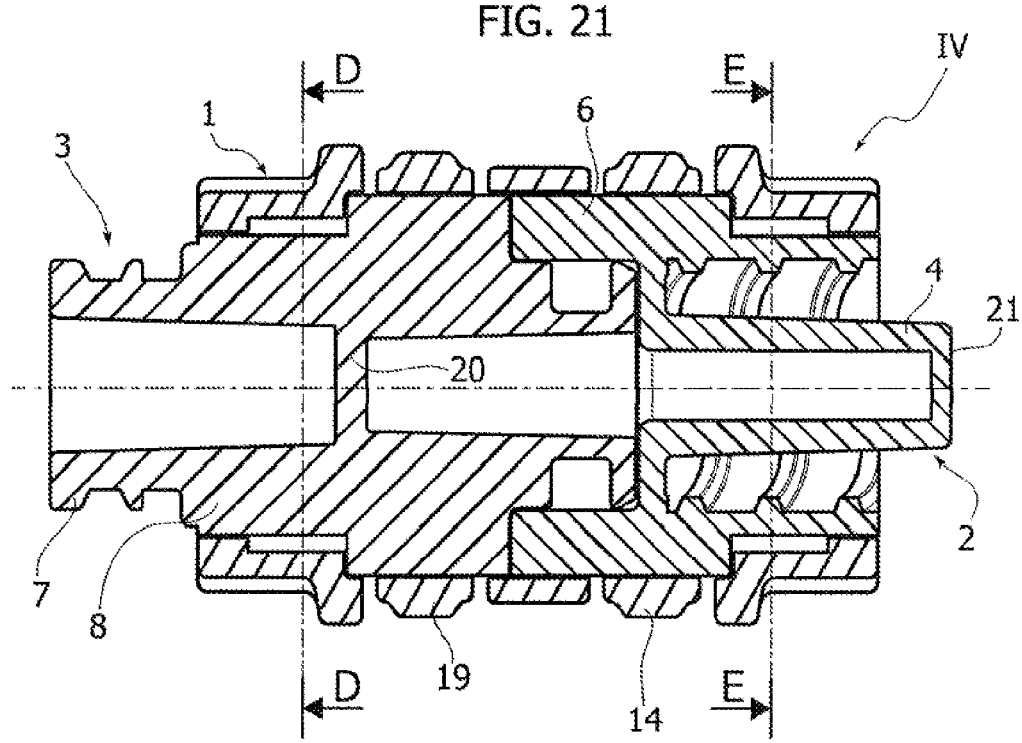
FIG. 21 is an axial section view according to the line C-C of FIG. 20.
Figure 23:
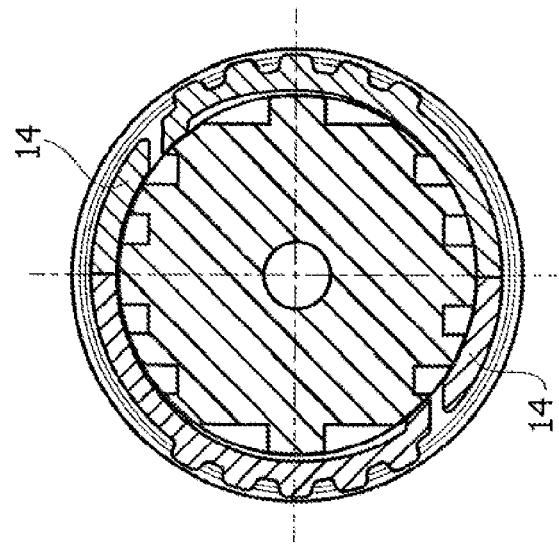
FIG. 23 is a cross sectional view along line A-A of FIG. 20.
Figure 22:
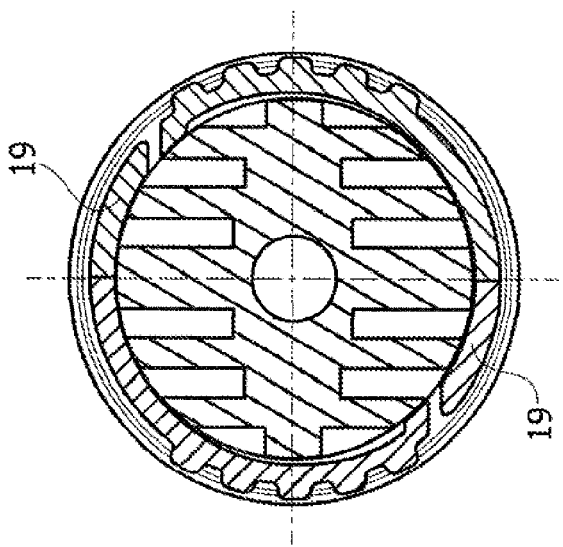
FIG. 22 is a cross sectional view along line B-B of FIG. 20.
Figure 24:
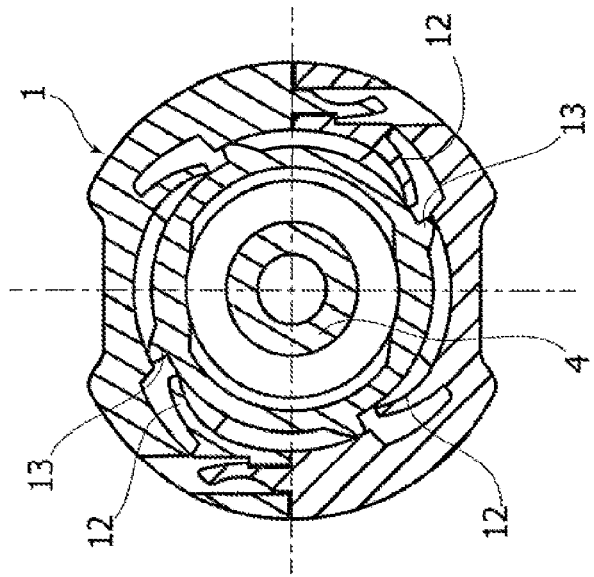
FIG. 24 is a cross sectional view along line D-D of FIG. 21.
Figure 25:
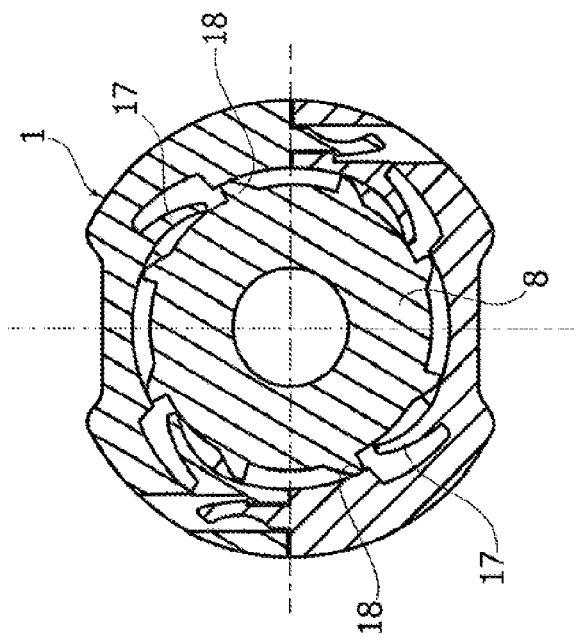
FIG. 25 is a cross sectional view along line E-E of FIG. 21.
Figure 27:
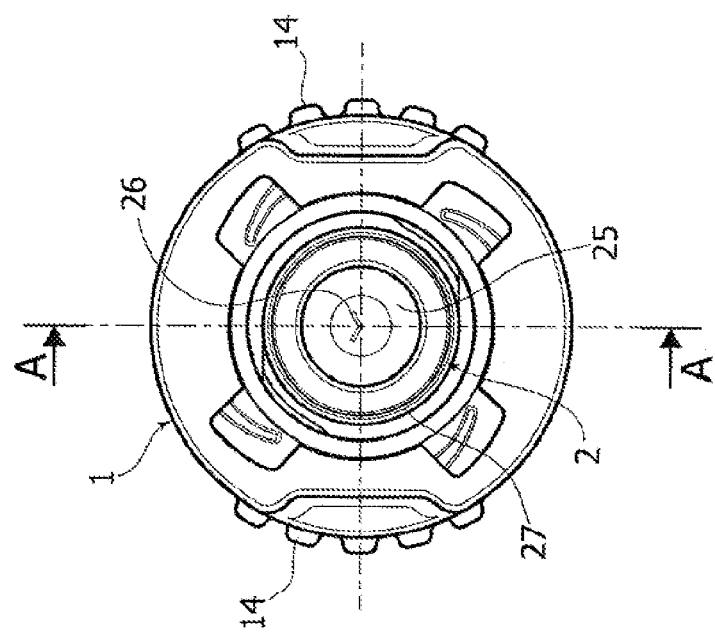
FIG. 27 is an end view of the fitting of FIG. 26.
Figure 26:
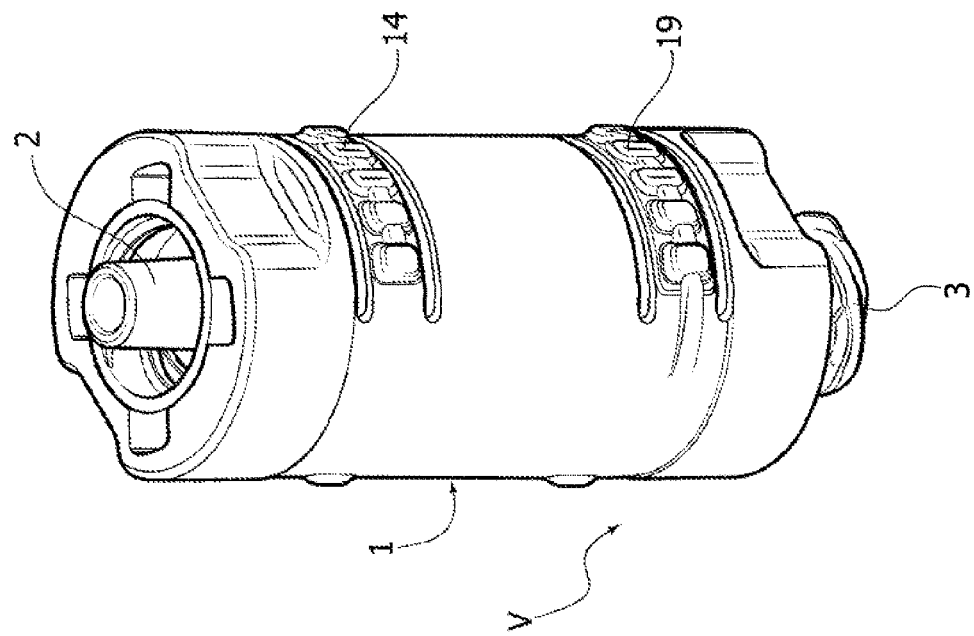
FIG. 26 is a schematic perspective view of a fifth embodiment of the fitting according to the invention.
Figure 28:
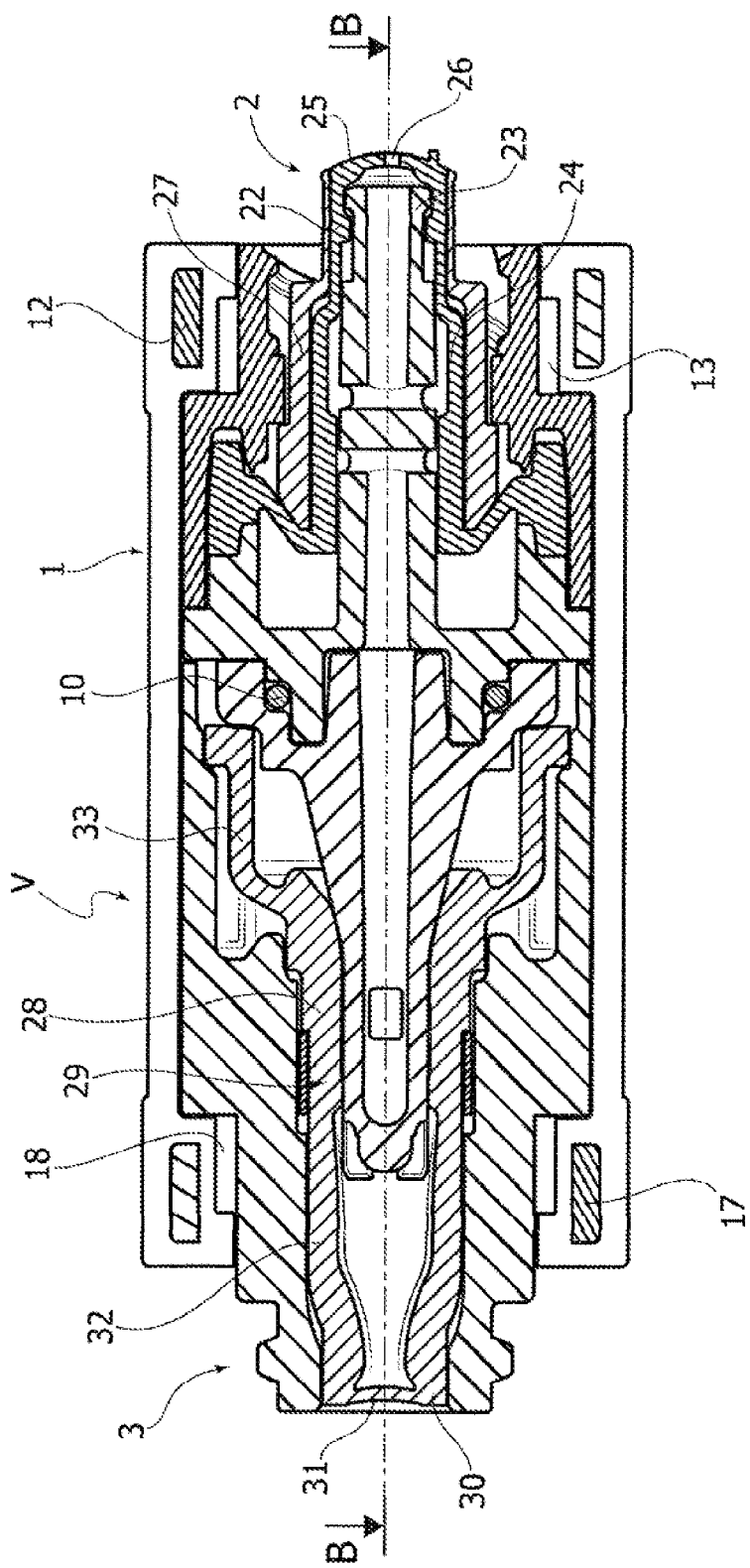
FIG. 28 is a sectional view along the line A-A of FIG. 27.
Figure 29:
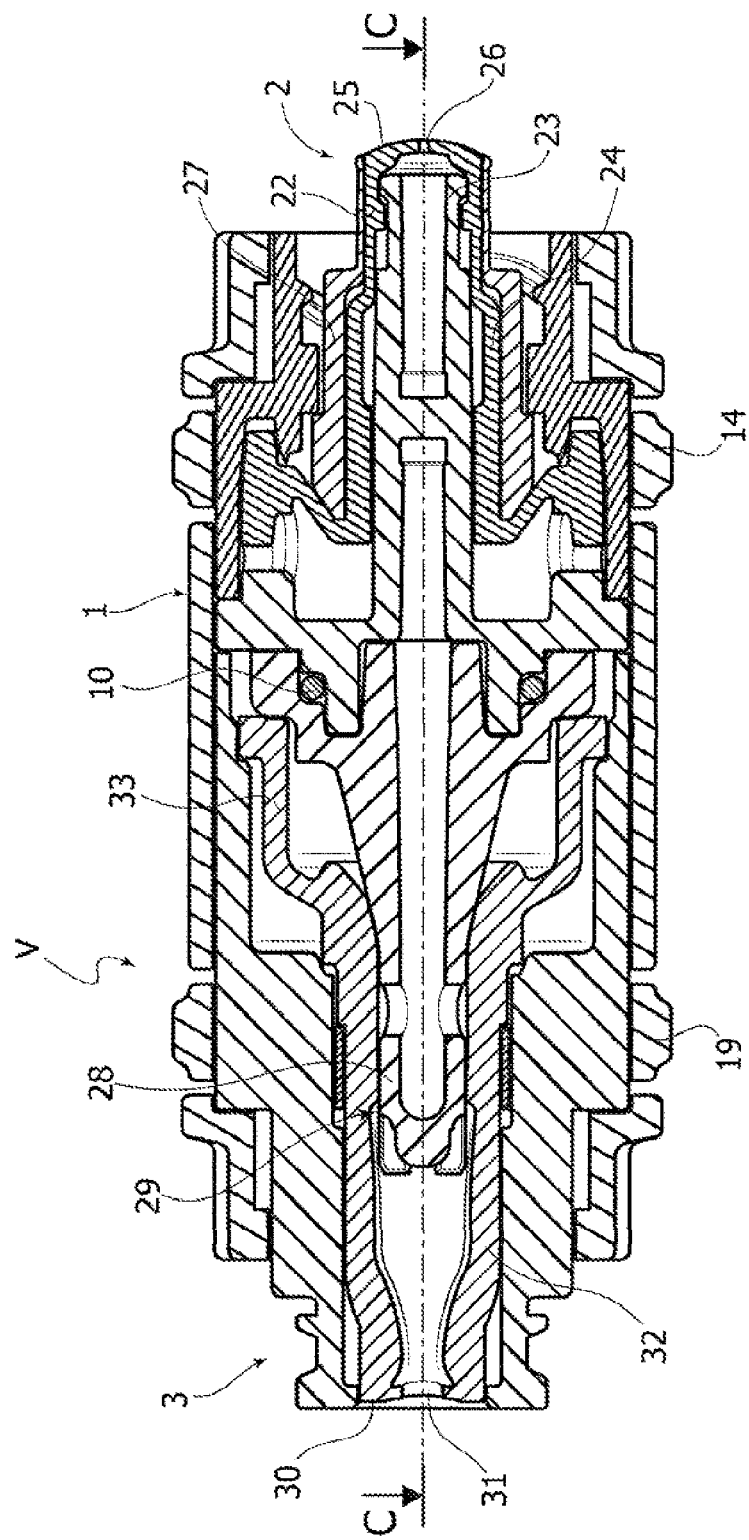
FIG. 29 is a sectional view along the line B-B of FIG. 28.

In the variant shown in FIGS. 20-25, the fitting, indicated as a whole with IV, is analogous to the connection I and only differs from it in the fact that it also does not define an open flow passage between the two connectors 2 and 3, whose communication is thus obstructed. In this case, the inner element 4 of the male connector 2 is closed by a transverse partition 21 (FIG. 21).

In the variant shown in FIGS. 26-29, the fitting, indicated as a whole with V, is tubular and the male 2 and female 3 connectors are valve connectors of the cleanable ("swabbable") type.

In particular, the male valve connector 2 generally corresponds to that described in the document US-2012/0271246 by the same Applicant: briefly, it comprises a tubular member 22 having an inlet 23 protruding from one end of the hollow body 1, an elastic hollow element 24 which surrounds the tubular member 22 and has an end wall 25 which normally closes the inlet 23 and is formed with a pre-cut 26. A collar 27 surrounds part of the elastic hollow element 24 and is axially movable due to the effect of the coupling of the valve connector 2 with a complementary female connector, inducing a tensile strain of the elastic hollow element 24 and opening the pre-cut 26 and therefore the flow passage through the tubular member 22.

The female connector valve 3 generally corresponds to that described in the document US-2009/0292274 by the same Applicant: briefly, it comprises an inner hollow pin 28 arranged axially within an intermediate sealing member 29, which is formed with an elastic head 30 having a pre-cut 31, with an elastic hollow element 32 in sealing contact with the hollow pin 28, and with an elastic thrust part 33 tending to maintain the elastic head 30 in a closed condition of the pre-cut 31. When the female connector 3 is coupled with a complementary male connector, the elastic head 30 is deformed so as to open the pre-cut 31, and therefore the flow passage through the hollow pin 28.

With this arrangement, the flow passage through the fitting V is normally closed, and only opens following the opening of one and/or the other of the valve connectors 2 and 3.

In this embodiment as well, the male valve fitting 2 and the female valve fitting 23 are each coupled in rotation with the casing 1 only in the screwing direction, through the respective unidirectional ratchets 12, 13 and 17, 18, and are freely rotatable in the opposite unscrewing direction. They may also possibly be rendered voluntarily integral in rotation with the body 1 in the unscrewing direction as well, acting on the elastically yielding segments 14, 19 of the body 1, if present, similarly to the other embodiments described above.

Of course, the details of construction and the embodiments may be varied widely with respect to those described and illustrated, without departing from the scope of the present invention as defined in the following claims. For example, in the case of the fitting V, one or the other of the valve connectors 2, 3 could be replaced by a non-valvular fitting.

The invention claimed is:

1. A tubular fitting for medical fluid lines, comprising:
  a hollow body within which a male connector accessible at one end of the body and a female connector accessible at the other end of the body, are coaxially housed,
  first unidirectional coupling means to lock in rotation the male connector with respect to the body in a direction corresponding to a screwing of said male connector and a complementary female connector to be coupled therewith, and to enable free rotation of the male connector in the opposite direction,
  second unidirectional coupling means being provided to lock in rotation the female connector with respect to the body in a direction corresponding to the screwing of said female connector and a complementary male connector to be coupled therewith, and to enable free rotation of the female connector in the opposite direction, and
  wherein said male and female connectors are coupled together in a mutually rotary fashion with the interposition of an O-ring, and said male and female connectors are in communication with each another to define an open flow passage through the fitting.

2. A fitting according to claim 1, further comprising first locking means designed to be positively operated to lock in rotation one of said male connector or female connector, relative to the body in said opposite direction.

3. A fitting according to claim 2, further comprising second locking means designed to be positively operated to lock in rotation the other of said female connector and male connector, relative to the body in said opposite direction.

4. A fitting according to claim 1, wherein said first and second unidirectional coupling means comprise respective ratchet teeth.

5. A fitting according to claim 3, wherein said first and second locking means comprise respective elastically yielding segments of the body, designed to engage corresponding peripheral teeth of said male connector and female connector, respectively.

6. A fitting according to claim 1, wherein the communication between said male and female connectors is obstructed.

7. A fitting according to claim 6, wherein at least one of said male or female connectors has a transverse partition for closing the flow through said fitting.

8. A fitting according to claim 1, wherein the male connector is a valve connector.

9. A fitting according to claim 8, wherein the male connector comprises a tubular member having an inlet, an elastic hollow element that surrounds said tubular member and has an end wall that closes said inlet of the tubular member and is formed with a pre-cut, and a collar axially displaceable to cause a tensile strain of the elastic hollow element elastic so as to open said pre-cut.

10. A fitting according to claim 1, wherein the female connector is a valve connector.

11. A fitting according to claim 10, wherein the female connector comprises an inner hollow pin arranged axially within an intermediate sealing member having an elastic head formed with a pre-cut, an elastic hollow element in sealing contact with the hollow pin and an elastic thrust part tending to maintain the elastic head in a closed condition of said pre-cut.

12. A tubular fitting for medical fluid lines, comprising:
  a hollow body within which a male connector accessible at one end of the body and a female connector accessible at the other end of the body, are coaxially housed, first unidirectional coupling means to lock in rotation the male connector with respect to the body in a direction corresponding to a screwing of said male connector and a complementary female connector to be coupled therewith, and to enable free rotation of the male connector in the opposite direction, second unidirectional coupling means being provided to lock in rotation the female connector with respect to the body in a direction corresponding to the screwing of said female connector and a complementary male connector to be coupled therewith, and to enable free rotation of the female connector in the opposite direction, and wherein said male and female connectors are coupled together in a mutually rotary fashion with the interposition of an O-ring, and the communication between said male and female connectors is obstructed.

13. A fitting according to claim 12, wherein at least one of said male or female connectors has a transverse partition for closing the flow through said fitting.

14. A fitting according to claim 12, wherein the male connector is a valve connector.

15. A fitting according to claim 12, wherein the male connector comprises a tubular member having an inlet, an elastic hollow element that surrounds said tubular member and has an end wall that closes said inlet of the tubular member and is formed with a pre-cut, and a collar axially displaceable to cause a tensile strain of the elastic hollow element elastic so as to open said pre-cut.

16. A fitting according to claim 12, wherein the female connector is a valve connector.

17. A fitting according to claim 16, wherein the female connector comprises an inner hollow pin arranged axially within an intermediate sealing member having an elastic head formed with a pre-cut, an elastic hollow element in sealing contact with the hollow pin and an elastic thrust part tending to maintain the elastic head in a closed condition of said pre-cut.

* * * * *